(12) United States Patent
Fliri et al.

(10) Patent No.: US 7,056,922 B2
(45) Date of Patent: Jun. 6, 2006

(54) ACYLAMINO CYCLOPROPANE DERIVATIVES

(75) Inventors: Anton F. J. Fliri, Stonington, CT (US); Anthony R. Reinhold, Mystic, CT (US)

(73) Assignee: Pfizer Inc, New York, NY (US)

(*) Notice: Subject to any disclaimer, the term of this patent is extended or adjusted under 35 U.S.C. 154(b) by 0 days.

(21) Appl. No.: 10/629,220

(22) Filed: Jul. 29, 2003

(65) Prior Publication Data
US 2004/0029876 A1 Feb. 12, 2004

Related U.S. Application Data

(63) Continuation of application No. 09/973,615, filed on Oct. 9, 2001, now abandoned.

(60) Provisional application No. 60/251,117, filed on Dec. 4, 2000.

(51) Int. Cl.
*A61K 31/506* (2006.01)
*A61K 31/495* (2006.01)
*C07D 295/155* (2006.01)
*C07D 403/12* (2006.01)

(52) U.S. Cl. ............ 514/252.14; 514/253.01; 514/255.03; 514/256; 514/249; 514/331; 544/295; 544/365; 544/393; 544/335; 544/349; 546/234

(58) Field of Classification Search ............ 544/295, 544/365, 393; 514/252.14, 253.01, 255.03
See application file for complete search history.

(56) References Cited

U.S. PATENT DOCUMENTS
5,872,119 A 2/1999 Wermuth et al.

FOREIGN PATENT DOCUMENTS
WO WO 9851671 11/1998

OTHER PUBLICATIONS

Reynolds, Drugs vol. 51, p. 7-11 (1996).*
TenBrink, Annual Reports in Medicinal Chemistry, vol. 29, p. 43-51 (1994).*
Romero, Arthur G. et al: "Synthesis of Metabolically Stable Arylpiperazine 5-HTIA Receptor Agonists" Bioorg. Med. Chem. Lett. (1992), 2(12), 1703-6, XP001056751.
Norman M H et al., "Effects of Linking Bridge Modifications on the Antipsychotic Profile of Some Phthalimide and Isoindolinone Derivatives" Journal of Medicinal Chemistry, American Chemical Society, Washington, US, vol. 39, No. 1, 1996, pp. 149-157, XP000982309 ISSN: 0022-2623.
Emilien, Gerard et al: "Dopamine D3 agonists" Expert Opinion on Therapeutic Patents (2001), 11(11), 1713-1728, XP001057496.

* cited by examiner

*Primary Examiner*—Emily Bernhardt
(74) *Attorney, Agent, or Firm*—Steve T. Zelson; Jolene W. Appleman

(57) ABSTRACT

A compound of the formula

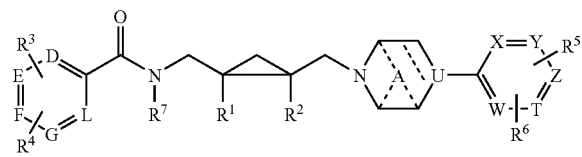

(I)

wherein D, E, F, G, L, T, W, X, Y, Z, U, A, $R^1$, $R^2$, $R^3$, $R^4$, $R^5$, $R^6$ $R^7$ are as defined in the specification, pharmaceutical compositions thereof, and methods of use to treat diseases and as D3 receptor modulators.

11 Claims, No Drawings

ACYLAMINO CYCLOPROPANE DERIVATIVES

CROSS REFERENCE TO RELATED APPLICATIONS

The present application is a continuation of U.S. Ser. No. 09/973,615 filed Oct. 9, 2001 now abandoned which claims benefit of U.S. Provisional Application No. 60/251,117 filed Dec. 4, 2000.

BACKGROUND OF THE INVENTION

The present invention relates to novel acylamino cyclopropane derivatives, processes for their preparation, pharmaceutical compositions containing them and their use as modulators of dopamine D3 receptors and for the treatment of anxiety, psychosis, substance abuse, Parkinsons disease, sexual dysfunction, and other central nervous system disorders.

The dopamine D3 receptor (the "D3 receptor") subtype has been identified (Sokoloff, P. et al., *Nature*, 1990, 347, 146). The D3 receptor is preferentially expressed in limbic brain regions such as the septal area and amygdala (Landwehrmeyer et al., *Mol. Brain Res.* (1993), 18 (1–2), 187–92). These regions are thought to be important brain areas for the regulation of cognition, motivation and emotion (Graeff et al., *Braz. J. Med. Biol. Res.* (1994), 27(10), 2453–6). The unique localization of D3 receptors and their differential recognition of various antipsychotics suggest that such receptors may play a major role in the etiology of schizophrenia.

Moreover, in patients suffering from Parkinson's disease (PD), repeated administration of levodopa, a dopamine precursor, results in progressive resumption of motor performances as well as in development of abnormal involuntary movements, suggesting sensitization to the drug. In a rat model of PD, it was shown that the unexpected appearance of the dopamine D3 receptor in the denervated caudate putamen, an area from which it is normally absent, accounts for the sensitization process: sensitization occurs and declines with the same time course and sensitization is blocked by a preferential D3 receptor antagonist; suggesting that dopamine D3 receptor antagonists may be useful in therapy of PD. *Biomed. Health Res.* (2000), 26, "Molecular Biology Approach to Parkinson's Disease", edited by Jenner, P., 49–60.

It has been shown that a dopamine D3 receptor partial agonist reduced the response to cocaine cues in rats suggesting that D3 antagonists may be useful for the development of substance abuse therapies. Pilla et al., 1999, *Nature*, 440: 371–375. In addition, mice without functional D3 dopamine receptors were examined animal models for anxiety. *Physiol. Behav.* (1997), 1998, 63(1), 137–141. The authors interpreted their results as indicative of reduced anxiety in mice without D3 receptos, suggesting that D3 dopamine receptor modulators may be useful for treatment of anxiety.

It has also been was shown that a structural congener of 7-OH-DPAT (7-Hydroxy Diisopropyl Amino Tetraline), primarily characterized as a D3 receptor selective ligand, produces a facilitation of male rat ejaculatory behavior, as evidenced by a dose-dependent decrease in the number of intromissions preceding ejaculation and in time to ejaculation, suggesting that dopamine D3 modulators may be useful in treatment of sexual dysfunction, e.g., for treatment of premature ejaculation. Ahlenius et al., *Pharmacol., Biochem. Behav.* (1995), 51(2/3), 545–7.

It is well accepted that dopamine receptors play an important role in the regulation of cardiovascular and kidney function. Recently, the peripheral actions of the D3 dopamine receptor subtype have also raised considerable interest as well because the dopamine D3 receptor subtype was identified in rat kidney and it has been shown in animal models that the disruption of D3 receptors at the gene level causes hypertension in mice and that D3 modulators effect sodium excretion in the rat kidney and the secretion of renin. Luippold et al., "Dopamine D3 Receptor Activation Modulates Renal Function in Anesthetized Rats", *Naunyn-Schmiedeberg's Arch. Pharmacol.* (1998), 358(6), 690–693.

Thus, dopamine D3 receptor modulators may also provide therapeutic potential as diuretics or anti-diuretics, treatment of urinary incontinence and in treatment of various cardiovascular pathological conditions, including hypertension. See, e.g., Asico, et al., *J. Clin. Invest.*, 1998, 102(3), 493–498; Luippold et al., *Acta Physiol. Scand.*, 2000, 168, 219–223.

Compounds of formula (I), which have described below, have been found to exhibit greater affinity for D3 receptor than for the dopamine D2 receptor ("D2 receptor"), and are expected to be useful in the treatment of diorders that can be treated by modulating the D3 receptor, such as psychotic conditions, anxiety, depression, Parkinson's disease, substance abuse, sexual dysfunction, and movement disorders.

SUMMARY OF THE INVENTION

This invention relates to compounds of the formula

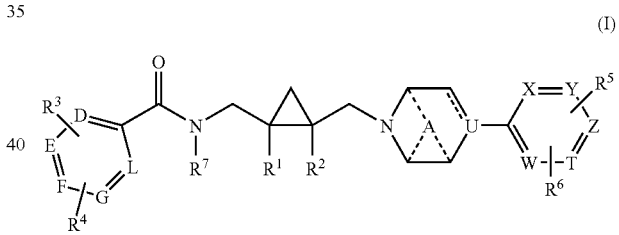

(I)

wherein D, E, F, G, L, T, W, X, Y and Z are each, independently, N or CH;

U is $CR^8$ or N when U is single bonded to both carbons adjacent to it in the nitrogen containing ring of which it is a member, and U is C when U is double bonded to one of the carbons that is adjacent to it in the nitrogen containing ring of which it is a member;

A is $(CH_2)_m$ wherein m is zero, one or two; $R^1$ and $R^2$ are selected, independently, from hydrogen, $(C_1-C_6)$ alkyl optionally substituted with from one to seven fluorine atoms, cyano, —$OR^9$, and —$CONHR^{10}$;

or $R^1$ and $R^2$, together with carbon atoms of the cyclopropyl ring to which they are attached, form a five or six membered saturated or unsaturated monocyclic ring containing from zero to four heteroatoms, wherein said heteroatoms are selected, independently, from oxygen, sulfur and nitrogen, with the proviso that there can not be two adjacent ring oxygen atoms, and wherein said ring can be optionally substituted with from one to three substituents independently selected from $(C_1-C_4)$ alkyl optionally substituted with from one to three fluorine atoms, $(C_1-C_4)$ alkoxy optionally substituted with from one to three fluorine atoms, cyano, nitro, halo, hydroxy, amino, $(C_1-C_4)$ alkylamino, di[$(C_1-C_6)$alkyl] amino, $(C_1-C_4)$ amidoamino and $(C_1-C_4)$ alkanoyl;

or one of $R^1$ and $R^2$ forms, together with $R^7$, a five or six membered saturated or unsaturated monocyclic ring containing from zero to four heteroatoms, wherein said heteroatoms are selected, independently, from oxygen, sulfur and nitrogen, with the proviso that there can not be two adjacent ring oxygen atoms, and wherein said ring can be optionally substituted with from one to three substituents independently selected from $(C_1-C_4)$ alkyl optionally substituted with from one to three fluorine atoms, $(C_1-C_4)$ alkoxy optionally substituted with from one to three fluorine atoms, cyano, nitro, halo, hydroxy, amino, $(C_1-C_4)$ alkylamino, di[$(C_1-C_6)$alkyl] amino, $(C_1-C_4)$ amidoamino and $(C_1-C_4)$ alkanoyl;

$R^3$ and $R^4$ are selected, independently, from hydrogen, halo, $(C_1-C_6)$ alkyl optionally substituted with from one to seven fluorine atoms, cyano, hydroxy, —CONHR, —OR$^{12}$, —NR$^{13}$R$^{14}$ and —COR$^{15}$.

or one of $R^3$ and $R^4$ forms, together with $R^7$, a five or six membered aromatic or nonaromatic ring containing from one to four heteroatoms, wherein said heteroatoms are selected, independently, from oxygen, sulfur and nitrogen, with the proviso that there can not be two adjacent ring oxygen atoms, and wherein said ring can be optionally substituted with from one to three substituents independently selected from $(C_1-C_4)$ alkyl optionally substituted with from one to three fluorine atoms, $(C_1-C_4)$ alkoxy optionally substituted with from one to three fluorine atoms, cyano, nitro, halo, hydroxy, amino, $(C_1-C_4)$ alkylamino, di[$(C_1-C_6)$alkyl] amino, $(C_1-C_4)$ amidoamino and $(C_1-C_4)$ alkanoyl;

$R^5$ and $R^6$ are selected, independently, from hydrogen, halo, $(C_1-C_6)$ alkyl optionally substituted with from one to seven chlorine atoms, cyano, hydroxy, —CONHR$^{16}$, —OR$^{17}$, —NR$^{18}$R$^{19}$, and —COR$^{20}$;

$R^7$ is hydrogen, $(C_1-C_6)$alkyl optionally substituted with from one to seven fluorine atoms, or aryl selected from phenyl and naphthyl, wherein said aryl can be optionally substituted with from one to three substituents independently selected from $(C_1-C_4)$ alkyl optionally substituted with from one to three fluorine atoms, $(C_1-C_4)$ alkoxy optionally substituted with from one to three fluorine atoms, cyano, nitro, halo, hydroxy, amino, $(C_1-C_4)$ alkylamino, di[$(C_1-C_6)$alkyl] amino, $(C_1-C_4)$ amidoamino and $(C_1-C_4)$ alkanoyl;

or $R^7$ can form a ring with $R^1$ or $R^2$, as described in the above definition of $R^1$ and $R^2$;

or $R^7$ can form a ring with $R^3$ or $R^4$, as described in the above definition of $R^3$ and $R^4$;

$R^8$ is selected from hydrogen, cyano, $(C_1-C_6)$ alkyl optionally substituted with from one to seven fluorine atoms, —OR$^9$, and —CONHR$^{10}$;

$R^9$, $R^{10}$, $R^{11}$, $R^{12}$, $R^{13}$, $R^{14}$, $R^{16}$, $R^{17}$, $R^{18}$ and $R^{19}$ are selected, independently, from hydrogen, $(C_1-C_6)$alkyl optionally substituted with from one to seven fluorine atoms, aryl and heteroaryl, wherein said aryl is selected from phenyl and naphthyl and said heteroaryl is selected from four to six membered monocyclic aromatic rings containing from one to four heteroatoms (nonlimiting examples of such rings are furyl, thienyl, pyrrolyl, oxazolyl, thiazolyl, imidazolyl, oxadiazolyl, thiadiazolyl, pyridyl, triazolyl, triazinyl, pyridazyl, pyrimidinyl and pyrazolyl) and eight to twelve membered bicyclic aromatic rings containing from one to five heteroatoms, wherein said heteroatoms are selected, independently, from oxygen, sulfur and nitrogen, with the proviso that there can not be two adjacent ring oxygen atoms, and wherein said aryl and heteroaryl rings can optionally be substituted one or more substitituents, preferably with from zero to two substituents, independently selected from $(C_1-C_4)$ alkyl optionally substituted with from one to three fluorine atoms, $(C_1-C_4)$ alkoxy optionally substituted with from one to three fluorine atoms, cyano, nitro, halo, hydroxy, amino, $(C_1-C_4)$ alkylamino, di[$(C_1-C_6)$ alkyl] amino, $(C_1-C_4)$ amidoamino and $(C_1-C_4)$ alkanoyl;

$R^{15}$ and $R^{20}$ are selected, independently, from NHR$^{21}$ and the group of radicals listed in the definition of $R^9$ through $R^{19}$; and $R^{21}$ is selected from the group of radicals listed in the definition of $R^9$ through $R^{19}$;

and the pharmaceutically acceptable salts thereof.

This invention also relates to a pharmaceutical composition for treating a disorder or condition selected from psychotic conditions (e.g., psychosis, schizophrenia, schizo-affective disorders, psychotic depression, mania, paranoid and delusional disorders), anxiety-related disorders (e.g., generalized anxiety disorder, post traumatic stress disorder, panic disorder, obsessive-compulsive disorder and phobias, including social phobia), mood disorders (e.g., cyclothymia, dysthymia, major depressive disorder, premenstrual syndrome, premenstrual dysphoric disorder, bipolar disorder, seasonal affective disorder), Parkinson's disease, hypertension, hypotension, urinary incontinence, chemical dependencies and addictions (e.g., dependencies on alcohol, cocaine, heroin, nicotine, benzodiazepines, phenobarbitol), sexual dysfunction (e.g., premature ejaculation, male erectile dysfunction) and movement disorders (e.g., drug induced and neurodegeneration based dyskinesias) in a mammal, including a human, comprising an amount of a compound of the formula I, as defined above, or a pharmaceutically acceptable salt thereof, that is effective in treating such disorder or condition, and a pharmaceutically acceptable carrier.

This invention also relates to a method of treating a disorder or condition selected from psychotic conditions (e.g., psychosis, schizophrenia, schizo-affective disorders, psychotic depression, mania, paranoid and delusional disorders), anxiety-related disorders (e.g., generalized anxiety disorder, post traumatic stress disorder, panic disorder, obsessive-compulsive disorder and phobias, including social phobia), mood disorders (e.g., cyclothymia, dysthymia, major depressive disorder, premenstrual syndrome, premenstrual dysphoric disorder, bipolar disorder, seasonal affective disorder), Parkinson's disease, hypertension, hypotension, urinary incontinence, chemical dependencies and addictions (e.g., dependencies on alcohol, cocaine, heroin, nicotine, benzodiazepines, phenobarbitol), sexual dysfunction (e.g., premature ejaculation, male erectile dysfunction) and movement disorders (e.g., drug induced and neurodegeneration based dyskinesias) in a mammal, including a human, comprising administering to said mammal an amount of a compound of the formula I, as defined above, or a pharmaceutically acceptable salt thereof, that is effective in treating such disorder or condition.

This invention also relates to a pharmaceutical composition for treating a disorder or condition selected from psychotic conditions (e.g., psychosis, schizophrenia, schizo-affective disorders, psychotic depression, mania, paranoid and delusional disorders), anxiety-related disorders (e.g., generalized anxiety disorder, post traumatic stress disorder, panic disorder, obsessive-compulsive disorder and phobias, including social phobia), mood disorders (e.g., cyclothymia, dysthymia, major depressive disorder, premenstrual syndrome, premenstrual dysphoric disorder, bipolar disorder, seasonal affective disorder), Parkinson's disease, hypertension, hypotension, urinary incontinence, chemical dependencies and addictions (e.g., dependencies on alcohol, cocaine, heroin, nicotine, benzodiazepines, phenobarbitol), sexual dysfunction (e.g., premature ejaculation, male erectile dysfunction) and movement disorders (e.g., drug induced and neurodegeneration based dyskinesias) in a mammal, including a human, comprising a D3 receptor binding modulating effective amount of a compound of the formula I, as defined above, or a pharmaceutically acceptable salt thereof, and a pharmaceutically acceptable carrier.

This invention also relates to a method of treating a disorder or condition selected from psychotic conditions (e.g., psychosis, schizophrenia, schizo-affective disorders, psychotic depression, mania, paranoid and delusional disorders), anxiety-related disorders (e.g., generalized anxiety disorder, post traumatic stress disorder, panic disorder, obsessive-compulsive disorder and phobias, including social phobia), mood disorders (e.g., cyclothymia, dysthymia, major depressive disorder, premenstrual syndrome, premenstrual dysphoric disorder, bipolar disorder, seasonal affective disorder), Parkinson's disease, hypertension, hypotension, urinary incontinence, chemical dependencies and addictions (e.g., dependencies on alcohol, cocaine, heroin, nicotine, benzodiazepines, phenobarbitol), sexual dysfunction (e.g., premature ejaculation, male erectile dysfunction) and movement disorders (e.g., drug induced and neurodegeneration based dyskinesias) in a mammal, including a human, comprising administering to said mammal a D3 receptor binding modulating effective amount of a compound of the formula I, as defined above, or a pharmaceutically acceptable salt thereof.

This invention also relates to a pharmaceutical composition for treating a disorder or condition, treatment of which can be effected or facilitated by modulating binding activity at the dopamine D3 receptor, in a mammal, including a human, comprising an amount of a compound of the formula I, as defined above, or a pharmaceutically acceptable salt thereof, that is effective in treating such disorder or condition, and a pharmaceutically acceptable carrier.

This invention also relates to a method of treating a disorder or condition, treatment of which can be effected or facilitated by modulating binding activity at the dopamine D3 receptor, in a mammal, including a human, comprising administering to said mammal an amount of a compound of the formula I, as defined above, or a pharmaceutically acceptable salt thereof, that is effective in treating such disorder or condition.

This invention also relates to a pharmaceutical composition for treating a disorder or condition, treatment of which can be effected or facilitated by modulating binding activity at the dopamine D3 receptor, in a mammal, including a human, comprising a D3 receptor binding modulating effective amount of a compound of the formula I, as defined above, or a pharmaceutically acceptable salt thereof, and a pharmaceutically acceptable carrier.

This invention also relates to a method of treating a disorder or condition, treatment of which can be effected or facilitated by modulating binding activity at the dopamine D3 receptor, in a mammal, including a human, comprising administering to said mammal a D3 receptor binding modulating effective amount of a compound of the formula I, as defined above, or a pharmaceutically acceptable salt thereof.

This invention also relates to the use of a compound of the formula I, or a pharmaceutically acceptable salt thereof, in the manufacture of a medicament for the treatment of a disorder or condition the treatment of which can be effected or facilitated by modulating binding to the dopamine D3 receptor.

Compounds of formula I may contain chiral centers and therefore may exist in different enantiomeric and diastereomeric forms. Hence, the compounds can exist in separated (+)- and (−)-optically active forms, as well as mixtures thereof. This invention relates to all optical isomers and all other stereoisomers of compounds of the formula I, and to racemic and other mixtures thereof. Individual isomers can be obtained by known methods, such as optical resolution, optically selective reaction, or chromatographic separation in the preparation of the final product or its intermediate.

Certain of the substituted heteroaryl ring systems included in compounds of the formula I may exist in one or more tautomeric forms. The present invention includes within its scope all such tautomeric forms, including mixtures of such forms.

In so far as the compounds of formula I of this invention are basic compounds, they are capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate))salts.

Also included within the scope of this invention are solvates and hydrates of compounds of formula I and their pharmaceutically acceptable salts. The present invention includes within its scope all possible stoichiometric and non-stoichiometric forms.

The present invention also includes isotopically labelled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$ isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like.

The term "alkoxy", as used herein, unless otherwise indicated, means "alkyl-O—", wherein "alkyl" is as defined above. Examples of "alkoxy" groups include, but are not limited to, methoxy, ethoxy, propoxy, butoxy and pentoxy.

The term "alkenyl", as used herein, unless otherwise indicated, includes unsaturated hydrocarbon radicals having one or more double bonds connecting two carbon atoms, wherein said hydrocarbon radical may have straight, branched or cyclic moieties or combinations thereof. Examples of "alkenyl" groups include, but are not limited to, ethenyl, propenyl, butenyl, pentenyl, and dimethylpentyl, and include E and Z forms where applicable.

The term "one or more substituents", as used herein, refers to a number of substituents that equals from one to the maximum number of substituents possible based on the number of available bonding sites.

The terms "halo" and "halogen", as used herein, unless otherwise indicated, include, fluoro, chloro, bromo and iodo.

The term "treating", as used herein, refers to reversing, alleviating, inhibiting the progress of, or preventing the disorder or condition to which such term applies, or preventing one or more symptoms of such condition or disorder. The term "treatment", as used herein, refers to the act of treating, as "treating" is defined immediately above.

Examples of the 5 and 6-membered heterocyclic groups referred to in the definition of compounds of the formula I include, but are not limited to, furyl, thienyl, pyrrolyl, oxazolyl, thiazolyl, imidazolyl, oxadiazolyl, thiadiazolyl, pyridyl, triazolyl, triazinyl, pyridazyl, pyrimidinyl and pyrazolyl.

The compounds of formula I can exist in the form of cis- and trans-isomers with respect to the configuration at the cyclopropane ring. Preferably, the compounds of the invention are in the Z (cis) configuration with respect to the cyclopropyl ring.

Other examples of preferred compounds of the formula I are those wherein $R^1$ and $R^2$ represent substituents selected from hydrogen, methyl, cyano, trifluoromethyl, and trifluoromethoxy. Other examples of preferred compounds of the formula I are those wherein $R^1$ and $R^2$ represent substituents selected from hydrogen and: $(C_1-C_6)$alkyl. Especially preferred are compounds of the formula I wherein $R^1$ and $R^2$ are both hydrogen.

Other examples of preferred compounds of the formula I are those wherein m is zero or two, in the case where m is two forming an azabicyclic ring system bridged either diagonally or directly across the ring system.

Other examples of preferred compounds of the formula I are those wherein X, Y, and T are carbon atoms and either one or both of W and Z are carbon or nitrogen, thus forming, for example, a phenyl, pyridyl or pyrimidyl ring.

More preferred compounds of the formula I are those wherein $R^5$ is selected from the group consisting of $(C_1-C_4)$ alkyl, Cl, F, CN, trifluoromethyl, —$OR^{17}$, and trifluoromethoxy.

Examples of specific compounds of this invention include the following compounds and their pharmaceutically acceptable salts:

[Z](+/−)2,6-Dimethyl-N-{2-[4-(3trifluoromethyl-phenyl)-piperazin-1-ylmethyl]-cyclopropylmethyl}-benzamide;

[Z](+/−)N-{2-[4-(2-tert-Butyl-6-trifluoromethyl-pyrimidin-4-yl)-piperazin-1-ylmethyl]-cyclopropylmethyl}-2,6-dimethyl-benzamide;

[E](+/−)2,6-Dimethyl-N-{2-[4-(3-trifluoromethyl-phenyl)-piperazin-1-ylmethyl]-cyclopropylmethyl}-benzamide;

[Z](+/−)N-{2-[4-(2-tert-Butyl-6-trifluoromethyl-pyrimidin-4-yl)-piperazin-1-ylmethyl]-cyclopropylmethyl}-4-chloro-benzamide;

[Z](+/−)N-{2-[4-(2-tert-Butyl-6-trifluoromethyl-pyrimidin-4-yl)-piperazin-1-ylmethyl]-cyclopropylmethyl}-2,4,6-trimethyl-benzamide;

[Z](+/−)N-{2-[4-(2-tert-Butyl-6-trifluoromethyl-pyrimidin-4-yl)-piperazin-1-ylmethyl]-cyclopropylmethyl}-3,4-dimethyl-benzamide;

[Z](+/−)N-{2-[4-(2-tert-Butyl-6-trifluoromethyl-pyrimidin-4-yl)-piperazin-1-ylmethyl]-cyclopropylmethyl}-3,5-dimethoxy-benzamide;

[Z](+/−)Thiophene-2-carboxylic acid {2-[4-(2-tert-butyl-6-trifluoromethyl-pyrimidin-4-yl)-piperazin-1-ylmethyl]-cyclopropylmethyl}-amide;

[Z](+/−)N-{2-[4-(2-tert-Butyl-6-trifluoromethyl-pyrimidin-4-yl)-piperazin-1-ylmethyl]-cyclopropylmethyl}-3-fluoro-benzamide;

[Z](+/−)1H-Pyrrole-2-carboxylic acid {2-[4-(2-tert-butyl-6-trifluoromethyl-pyrimidin-4-yl)-piperazin-1-ylmethyl]-cyclopropylmethyl}-amide;

[Z](+/−)N-{2-[4-(2-tert-Butyl-6-trifluoromethyl-pyrimidin-4-yl)-piperazin-1-ylmethyl]-cyclopropylmethyl}-2-methyl-benzamide;

[Z](+/−)N-{2-[4-(2-tert-Butyl-6-trifluoromethyl-pyrimidin-4-yl)-piperazin-1-ylmethyl]-cyclopropylmethyl}-2,3-dimethyl-benzamide;

[Z](+/−)N-{2-[4-(2-tert-Butyl-6-trifluoromethyl-pyrimidin-4-yl)-piperazin-1-ylmethyl]-cyclopropylmethyl}-3,4-dimethoxy-benzamide;

[Z](+/−)N-{2-[4-(2-tert-Butyl-6-trifluoromethyl-pyrimidin-4-yl)-piperazin-1-ylmethyl]-cyclopropylmethyl}-3,4,5-trimethoxy-benzamide;

[Z](+/−)N-{2-[4-(2-tert-Butyl-6-trifluoromethyl-pyrimidin-4-yl)-piperazin-1-ylmethyl]-cyclopropylmethyl}-isonicotinamide;

[Z](+/−) Naphthalene-1-carboxylic acid {2-[4-(2-tert-butyl-6-trifluoromethyl-pyrimidin-4-yl)-piperazin-1-ylmethyl]-cyclopropylmethyl}-amide;

[Z](+/−)N-{2-[4-(2-tert-Butyl-6-trifluoromethyl-pyrimidin-4-yl)-piperazin-1-ylmethyl]-cyclopropylmethyl}-4-fluoro-benzamide;

[Z](+/−)N-{2-[4-(2-tert-Butyl-6-trifluoromethyl-pyrimidin-4-yl)-piperazin-1-ylmethyl]-cyclopropylmethyl}-3-chloro-benzamide;

[Z](+/−)N-{2-[4-(2-tert-Butyl-6-trifluoromethyl-pyrimidin-4-yl)-piperazin-1-ylmethyl]-cyclopropylmethyl}-4-trifluoromethyl-benzamide;

[Z](+/−)Quinoline-3-carboxylic acid {2-[4-(2-tert-butyl-6-trifluoromethyl-pyrimidin-4-yl)-piperazin-1-ylmethyl]-cyclopropylmethyl}-amide;

[Z](+/−)N-{2-[4-(2-tert-Butyl-6-trifluoromethyl-pyrimidin-4-yl)-piperazin-1-ylmethyl]-cyclopropylmethyl}-3-cyano-benzamide;

[Z](+/−)N-{2-[4-(2-tert-Butyl-6-trifluoromethyl-pyrimidin-4-yl)-piperazin-1-ylmethyl]-cyclopropylmethyl}-2,6-dimethyl-benzamide;

[Z](+/−)N-{2-[4-(2-tert-Butyl-6-trifluoromethyl-pyrimidin-4-yl)-piperazin-1-ylmethyl]-cyclopropylmethyl}-2,4-difluoro-benzamide;

[Z](+/−)N-{2-[4-(2-tert-Butyl-6-trifluoromethyl-pyrimidin-4-yl)-piperazin-1-ylmethyl]-cyclopropylmethyl}-2,3-difluoro-benzamide;

[Z](+/−)N-{2-[4-(2-tert-Butyl-6-trifluoromethyl-pyrimidin-4-yl)-piperazin-1-ylmethyl]-cyclopropylmethyl}-2-trifluoromethyl-benzamide;

[Z](+/−)N-{2-[4-(2-tert-Butyl-6-trifluoromethyl-pyrimidin-4-yl)-piperazin-1-ylmethyl]-cyclopropylmethyl}-2,5-dichloro-benzamide;

[Z](+/−)N-{2-[4-(2-tert-Butyl-6-trifluoromethyl-pyrimidin-4-yl)-piperazin-1-ylmethyl]-cyclopropylmethyl}-2,3-dichloro-benzamide;

[Z](+/−) 4-Fluoro-naphthalene-1-carboxylic acid {2-[4-(2-tert-butyl-6-trifluoromethyl-pyrimidin-4-yl)-piperazin-1-ylmethyl]-cyclopropylmethy}-amide;

[Z](+/−)N-{2-[4-(2-tert-Butyl-6-trifluoromethyl-pyrimidin-4-yl)-piperazin-1-ylmethyl]-cyclopropylmethyl}-2,4-dimethyl-benzamide;

[Z](+/−)N-{2-[4-(2-tert-Butyl-6-trifluoromethyl-pyrimidin-4-yl)-piperazin-1-ylmethyl]-cyclopropylmethyl}-3-chloro-2-fluoro-benzamide;

[Z](+/−)N-{2-[4-(2-tert-Butyl-6-trifluoromethyl-pyrimidin-4-yl)-piperazin-1-ylmethyl]-cyclopropylmethyl}-2-chloro-4-fluoro-benzamide;

[Z](+/−)N-{2-[4-(2-tert-Butyl-6-trifluoromethyl-pyrimidin-4-yl)-piperazin-1-ylmethyl]-cyclopropylmethyl}-2-hydroxy-6-methyl-nicotinamide;

[Z](+/−)N-{2-[4-(2-tert-Butyl-6-trifluoromethyl-pyrimidin-4-yl)-piperazin-1-ylmethyl]-cyclopropylmethyl}-nicotinamide;

[Z](+/−)N-{2-[4-(2-tert-Butyl-6-trifluoromethyl-pyrimidin-4-yl)-piperazin-1-ylmethyl]-cyclopropylmethyl}-2,4-dichloro-benzamide;

[Z](+/−) 1H-Indole-5-carboxylic acid {2-[4-(2-tert-butyl-6-trifluoromethyl-pyrimidin-4-yl)-piperazin-1-ylmethyl]-cyclopropylmethyl}-amide; and N-{2-[4-(2-tert-Butyl-6-trifluoromethyl-pyrimidin-4-yl)-piperazin-1-ylmethyl]-cyclopropylmethyl}-4-diethylamino-benzamide.

Preferred salt forms of the compounds of this invention are the monohydrochloride and monomesylate salt forms.

A preferred use for D3 antagonists according to the present invention is in the treatment of anxiety and substance abuse. Preferred uses for D3 agonists according to the present invention are the treatment of dyskinetic disorders such as Parkinson's disease and treatment of sexual dysfunction such as for example premature ejaculation.

DETAILED DESCRIPTION OF THE INVENTION

In the reaction schemes and discussion that follow, unless otherwise indicated, A, D, E, F, G, L, T, U, W, X, Y, Z and $R^1$ through $R^{21}$ are defined as above.

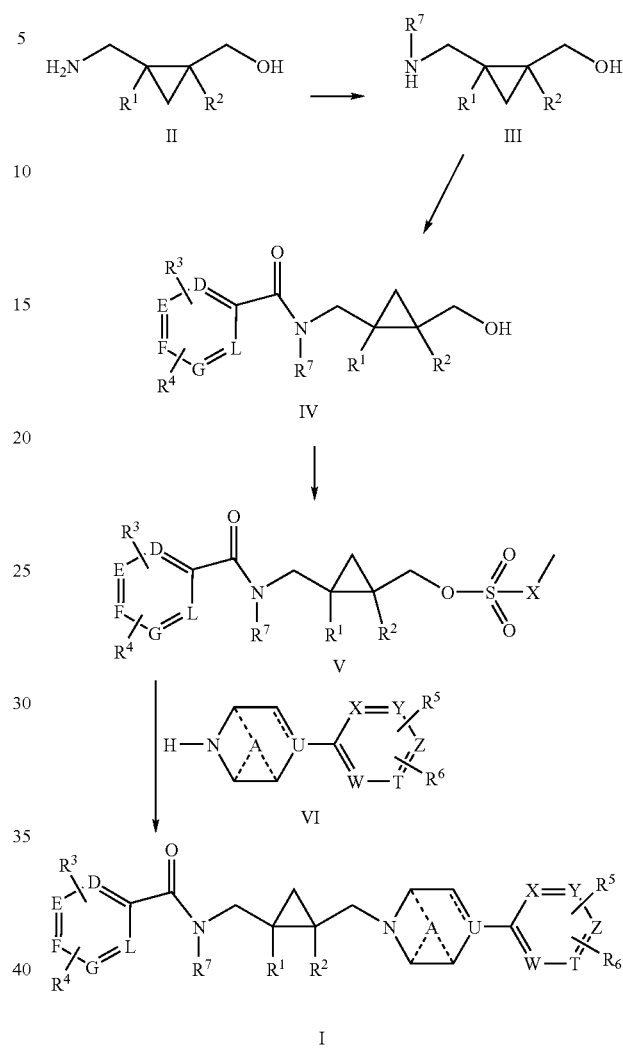

Referring to Scheme I, a compound of the formula III is formed by reacting a compound of the formula II with an alkyl aldehyde or dialkyl ketone, in the presence of a reducing agent such as sodium cyano borohydride, sodium triacetoxyborohydride, or an aluminum hydride or similar reagent, in a reaction inert solvent such as a lower alcohol, a cyclic or acyclic monoalkylamide or dialkylamide, acetonitrile, a cyclic or acyclic alkyl ether, or an aromatic solvent (e.g., benzene or toluene), preferably dichloroethane, at a temperature from about 0° C. to about 150° C., preferably at about ambient temperature.

Examples of cyclic and acyclic alkyl aldehydes and dialkyl ketones are the following: acetaldehyde, propionaldehyde, formaldehyde, cyclopropylaldehyde, acetone, cyclobutanone, cyclopentanone, and methyl ethyl ketone.

Examples of cyclic and acyclic alkylesters are the esters that correspond to the aldehydes listed above.

Examples of cyclic and acyclic monoalkylamides and dialkylamides are the following: formamide, acetamide, dimethylformamide, dimethylacetamide, pyrrolidinone, and N-methylpyrrolidinone.

Examples of cyclic and acyclic alkyl ethers are the following: diethyl ether, diisopropyl ether, tetrahydrofuran, dioxane and dibutyl ether.

Compounds of the formula II are described in the literature or may be prepared using methods described in *J. Med. Chem.* (1998), 31(12), 2304–15; *Synth. Commun.* (1999), 29(23), 4261–4268; *Tetrahedron* (1997), 53(28), 9497–9508; and *J. Prakt. Chem./Chem.-Ztg.* (1995), 337(1), 55–9, or using modifications of such methods that will be obvious to those of skill in the art.

The resulting compound of the formula III is then converted into a compound of the formula IV by reacting it with a compound of formula III'

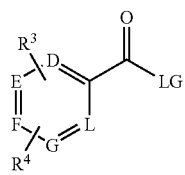

III' wherein LG represents a leaving group and is preferably selected from the group consisting of Cl, Br, N-hydroxy phthalimide, and N-hydroxy succinimide, but may also represent other leaving groups known in the art, or intermediates derived from the reaction of the appropriate substituted carboxylic acid with carbodiimides or acylating agents (e.g., activated esters such as, for example, para nitro phenyl esters, N-hydroxysuccinimide esters, imidazolides, acid chlorides and mixed anhydrides), to form a compound of the formula IV.

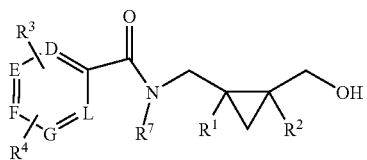

IV

This reaction is typically carried out in a reaction inert solvent such as a cyclic or acyclic monoalkylamide or dialkylamide, a cyclic or acyclic alkyl or dialkyl ether, or a mixture of two or more of the foregoing solvents, preferably dichloroethane or pyridine, at a temperature from about 0° C. to about 150° C., preferably at about ambient temperature of the reaction mixture. The presence of acid receptors (e.g., alkali carbonates or tertiary amines) are often helpful in promoting reaction.

Reaction of the compound of formula IV with a compound of the formula HX', wherein X'=Br, —SO$_3$CH$_3$, —SO$_3$CF$_3$, or —SO$_3$-aryl, wherein aryl is phenyl or naphthyl, yields an alkylating agent of the formula V

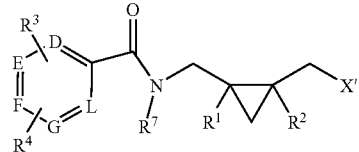

V wherein X' is defined as above.

When X' is bromine, the compound of formula IV is reacted with hydrobromic acid in benzene, tolune, dichoromethane or a similar reaction inert solvent, at a temperature from about ambient temperature to about the reflux temperature of the reaction mixture, preferably at about ambient temperature. When X' is an alkyl sulfonyl or aryl sulfonyl group, the compound of formula IV is reacted with an alkyl or aryl sulfonyl chloride or anhydride. This reaction is typically carried out at a temperature from about −20° C. to about ambient temperature, preferably at about 0° C., in a reaction inert solvent such as a chlorinated (C$_1$–C$_6$) alkane, a cyclic or acyclic alkyl ether, tetrahydrofuran (THF), methylene chloride, preferably methylene chloride, in the presence of a base such as triethylamine, diisopropylethylamine, or potassium or sodium carbonate, preferably diisopropylethylamine.

Reaction of the alkylating agent of formula V with a compound of the formula VI

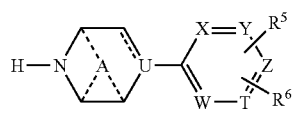

VI yeilds the desired compound of formula I. This reaction is typically carried out in a reaction inert solvent such as a lower alcohol, a cyclic or acyclic alkyl ester, a cyclic or acyclic alkyl ketone, a cyclic or acyclic monoalkylamide or dialkylamide, acetonitrile, a cyclic or acyclic alkyl ether or a mixture of two or more of the foregoing solvents. Preferably, the solvent is acetonitrile. The reaction temperature can range from about 0° C. to about 150° C., and is preferably about the reflux temperature of the reaction mixture. The presence of an acid receptor (e.g., alkali carbonates or tertiary amines) is often helpful in promoting the reaction.

Compounds of formula VI can be prepared as shown in Schemes 2, 3 and 4 below. Scheme 2 illustrates the synthesis of compounds of the formula VIA, a subgenus of the compounds of formula VI, wherein m is zero or one and U is N.

Scheme 2

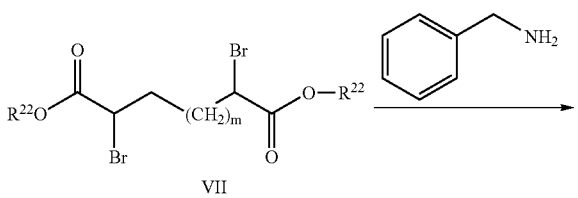

VII

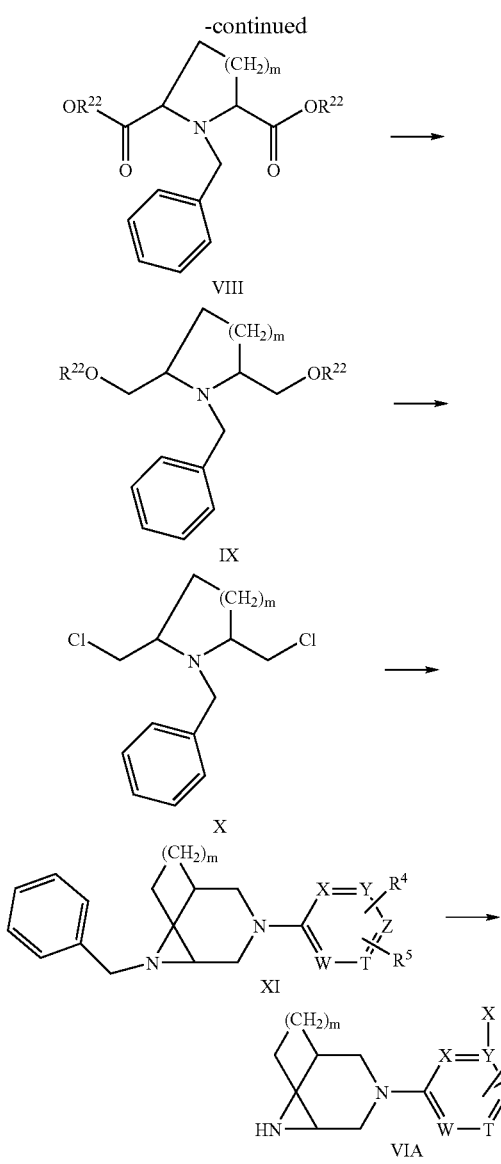

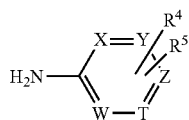

Referring to Scheme 2, a compound of the formula VII, wherein $R^{22}$ is $(C_1-C_6)$alkyl or hydrogen and m is zero or one, is allowed to react with benzylamine in the presence of a base such as, for example, diisopropylethylamine, triethylamine, sodium carbonate or potassium carbonate, to provide a compound of the general formula VIII. This reaction is typically carried out at a temperature ranging from about ambient temperature to about the reflux temperature of the solvent. Suitable solvents include dimethylformamide, acetonitrile, chloroform, dioxane, acetone, water, lower alcohols (e.g., propanol, ethanol, or methanol) and mixtures of one or more of the foregoing solvents. Reduction of the resulting compound of formula VIII yields the protected diol derivative of the formula IX. Suitable reducing agents include, for example, aluminum hydrides and borohydrides (e.g., lithium aluminum hydride, sodium borohydride, or lithium borohydride). This reaction is generally carried out at a temperature ranging from about ambient temperature to about the reflux temperature of the solvent, preferably at about ambient temperature, and the solvent is typically selected from the group consisting of lower alcohols, lower cyclic or acyclic alkyl ethers and dioxane. Preferably, the solvent is THF.

The compound of formula IX is then converted into the dichloride compound of the formula X by treating it with a reagent, such as, e.g., $SO_2Cl_2$, $POCl_3$ or a similar chlorinating reagent, in the absence of a solvent or in a halogenated solvent such as chloroform, carbon tetrachloride or methylene chloride, at a temperature ranging from about ambient temperature to about the reflux temperature of the reaction mixture, preferably at about the reflux temperature. The compound of formula X is then converted into the corresponding compound of formula XI by reacting it with an excess of a compound of the formula in the absence of a solvent, or in a solvent selected from N,N-dimethylformamide, dioxane, N,N-dimethylacetamide, pyrrolidinone, and mixtures of two or more of the foregoing solvents. The temperature for the reaction can range from about room temperature to about the reflux temperature of the reaction mixture.

Removal of the benzyl group from the compound of formula XI yields the desired compound of the formula VIA. This can be accomplished using hydrogen gas in presence of a catalyst selected from palladium on carbon, palladium hydroxide, platinum oxide and similar catalysts. This reaction is typically carried out in a solvent selected from lower cyclic or acyclic alkyl alcohols, lower cyclic or acyclic alkyl ethers, water, acetic acid, formic acid, hydrochloric acid, N,N-dimethylformamide and mixtures of two or more of the foregoing solvents, at a temperature ranging from about ambient temperature to about the reflux temperature of the reaction mixture, and at a hydrogen gas pressure ranging from about 0 to about about 5 atmospheres. Compounds of the general formula VIA can be converted into compounds of general formula I using the procedures described in Scheme I for converting compounds of the formula VI into those of the formula I.

Scheme 3 illustrates the synthesis of compounds of the formula I, wherein m is 0, 1, or 2 and U is —C—OH, —C—O—$(C_1-C_6)$alkyl, —CH, or —C—CN. Such compounds can be prepared as follows.

Scheme 3

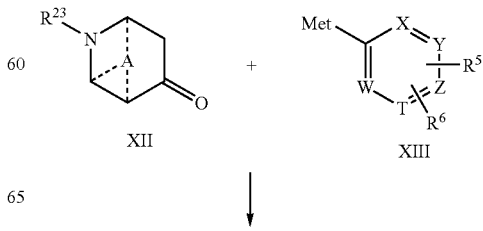

-continued

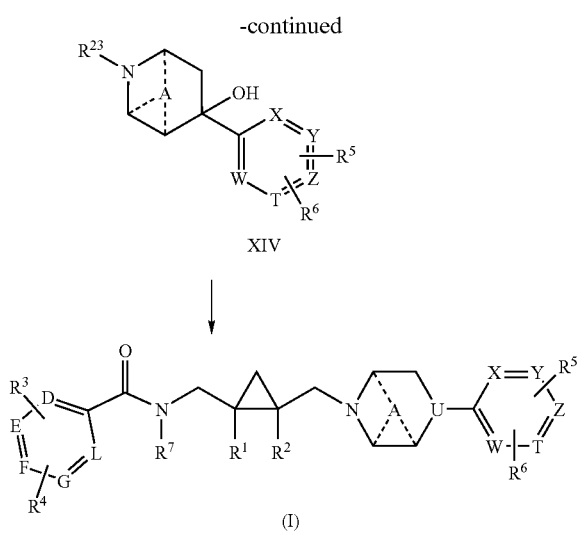

XIV

↓

(I)

Referring to Scheme 3, piperidine-4-one derivatives of the formula XII, wherein A is as defined above, and $R^{23}$ denotes a nitrogen protecting group, and which are commercially available or can be prepared using methods known to those of skill in the art, are reacted with an aryl or heteroaryl transferring reagent of the formula XIII, wherein Met denotes a metal such as, for example, $Li^+$, $Mg^{2+}$, $B(OH)_2$ or $Zn^{2+}$, to provide the corresponding intermediates of the formula XIV. These transformations can be carried out using procedures similar to those described in the following references: *Tetrahedron Lett.* (1995), 36 (18), 3099–102; *J. Pharm. Pharmacol.* (1985), 37 (2), 121–3; or *J. Org. Chem.* (1985), 50 (6), 852–6. The protecting groups $R^{23}$ can be any of the protecting groups commonly known and used for such reactions, including, e.g., benzyl, benzyloxycarbonyl, t-butoxycarbonyl, trityl groups, trifluoroacetyl, 2-chloroethoxycarbonyl and phatyl. Other such nitrogen protecting groups are referred to by Greene and Wuts, *Protective Groups in Organic Synthesis* (John Wiley & Sons, New York, 1991).

Compounds of the formula XIV can then be converted into compounds of formula I by removing the nitrogen protecting group ($R^{23}$) and, depending on the identity of U, further reacting the compound as indicated below. It is often convenient to remove such nitrogen protecting groups by hydrogenation or other deprotection procedures well known to those of skill in the art (e.g., removal of a t-butoxycarbonyl group via reaction with an acid), as described by Greene and Wuts, supra.

Compounds of general formula I wherein U is —CH can be prepared from the corresponding compounds of formula XIV via catalytic hydrogenation in presence of an acid, using methods well known to those of skill in the art. Compounds of formula XIV can be converted to compounds of the formula I wherein U is —CO—($C_1$–$C_6$)alkyl by alkylating the hydroxyl groups of the compounds of formula XIV. This can be accomplished by first forming an anion at the hydroxy group using a reagent such as, for example, a lithium, potassium or sodium alkane or an alkylamine derivative, in a solvent such as, for example, tetrahydrofuran, benzene, diethyl ether, dioxane or a similar solvent, or a mixture of two or more of the foregoing solvents, at a temperature ranging from about -20° C. to about the reflux temperature of the reaction mixture, preferably at about -20° C., and then treating the reaction mixture with an alkylating agent. Examples of suitable alkylating agents are ethyl iodide, methyl iodide, benzyl bromide and dimethylsulfate. The preferred alklyating agents are methyl iodide and benzyl bromide.

Similarly, compounds of formula I wherein U is —C—CN may be prepared by first forming a leaving group at the hydroxy group of the corresponding compounds of formula XIV, using a reagent such as, for example, hydrobromic acid, $SO_2Cl_2$ or $PBr_3$, or by treatment with an alkyl sulfonyl chloride such as, for example, methanesulfonyl chloride, trifluoromethanesulfonyl chloride or paratoluenesulfonyl chloride, in the presence of a base such as, for example, diisopropylethylamine, triethylamine, sodium carbonate or potassium carbonate. This reaction is typically carried out in a solvent selected from benzene, chlorinated alkanes and lower alkyl ethers, at a temperature ranging from about -20° C. to about the reflux temperature. Preferably, this reaction is carried out using methanesulfonyl chloride in methylene chloride at about -20° C. in the presence of diisopropylethylamine. The reaction mixture is then treated with a cyanide, such as, for example lithium, potassium, sodium or tetrabutyl amonium cyanide, in a solvent such as N,N-dimethylformamide, acetonitrile, chloroform, dioxane, acetone, water, or a lower alcohol (e.g., propanol, ethanol, methanol, etc.), or a mixture of two or more of the foregoing solvents, at a temperature ranging from about ambient temperature to about the reflux temperature of the reaction mixture. Preferably, the reaction is carried out in dimethylformamide at 60° C.

Removal of the benzyl group or other nitrogen protecting group from compounds of general formula XIV wherein U is nitrogen or —CH can be accomplished using hydrogen gas in presence of a catalyst selected from the group consisting of palladium on carbon, palladium hydroxide, platinum oxide and similar reagents, in a solvent or mixture of solvents selected from the group consisting of lower cyclic or acyclic alkyl alcohols, lower cyclic or acyclic alkyl ethers, water, acetic acid, formic acid, hydrochloric acid and N,N-dimethylformamide, and mixtures of two or more of the foregoing solvents, at a temperature ranging from about ambient temperature to about the reflux temperature of the reaction mixture, at a hydrogen gas pressure ranging from 0 to 5 atmospheres. Preferably, the reaction is carried out in ethanol or acetic acid at about 25° C.

Compounds of the formula I wherein U is —C—C(=O)NHR$^{10}$ can be prepared from the corresponding compounds wherein U is —C—CN by treating the cyano group with hydrochloric acid in a solvent selected from lower cyclic or acyclic alkyl alcohols, lower cyclic or acyclic alkyl ethers, water, acetic acid, formic acid, hydrochloric acid and N,N-dimethylformamide, and mixtures of two or more of the foregoing solvents, at a temperature ranging from about ambient temperature to about the reflux temperature of the reaction mixture, and then converting the resulting carboxylic acid into the corresponding —C(=O)NHR$^{10}$ derivative using methods that are well known to those of skill in the art and similar to the methods described above for forming compounds of the formula IV.

Compounds of the formula I wherein U is —C—($C_1$–$C_6$) alkyl can be prepared from the corresponding carboxylic acids (U=—COOH) by first converting the carboxylic acids into the corresponding aldehydes (U=—CHO) using methods well known to those of skill in the art and then treating the aldehydes with an alkyl transferring agent of the formula ($C_1$–$C_6$)alkyl-Met, wherein Met is a group such as $Li^+$, $Mg^{2+}$, $K^+$, $B(OH)_2$, or $Zn^{2+}$, also using methods well known to those of skill in the art (e.g., using an ethyl ether solvent and a temperature from about 0° C. to about ambient temperature, preferably at about 0° C.), to provide the corresponding hydroxyalkyl intermediates. The hydroxyalkyl intermediates are then reacted with an acid such as methanesulfonic acid, sulfuric acid, hydrochloric acid or trifluoromethanesulfonic acid to provide the unsaturated analogs (U=—C—($C_1$–$C_6$)alkene) of the desired compounds of formula I, and then hydrogenating such unsaturated compounds to form the desired compounds of the formula I. The hydrogenation is accomplished using hydrogen gas in the presence of a catalyst such as palladium, palladium hydroxide or platinum hydroxide, in a solvent such as ethanol, methanol, acetic acid, or water, or mixtures of two or more of the foregoing solvents, at a temperature from about ambient temperature to about the reflux temperature.

Compounds of formula I have been found to exhibit affinity for dopamine D3 receptors, and are expected to be useful in the treatment of disease states which require. modulation of such receptors, such as psychotic conditions. Compounds of formula I have also been found to have greater affinity for dopamine D3 than for D2 receptors. The therapeutic effect of currently available antipsychotic agents (neuroleptics) is generally believed to be mediated via blockade of D2 receptors. However, this mechanism is also thought to be responsible for undesirable extrapyramidal side effects (eps) associated with many neuroleptic agents. It has been suggested that blockade of the recently characterised dopamine D3 receptor may give rise to beneficial antipsychotic activity without significant eps. (See, e.g., Sokoloff et al., *Nature*, 1990; 347: 146–15 1; and Schwartz et al., *Clinical Neuropharmacology*, Vol 16, No. 4, 295–314, 1993).

Preferred compounds of the present invention are therefore those that have higher affinity for dopamine D3 than dopamine D2 receptors (such affinity can be measured using standard methodology for example using cloned dopamine receptors). Said compounds may advantageously be useful as dopamine D3 receptor antagonists, while others may be agonists or partial agonists. The functional activity of compounds of the invention (i.e., whether they are antagonists, agonists or partial agonists) can be readily determined using the test methods described hereinafter.

D3 antagonists are useful as antipsychotic agents, for example, in the treatment of schizophrenia, schizo-affective disorders, psychotic depression, mania, paranoid and delusional disorders. Furthermore, they have utility as adjunct therapy in Parkinson's Disease, particularly with compounds such as L-DOPA and possibly dopaminergic agonists, to reduce the side effects experienced with these treatments on long term use (see Schwartz et al., *Brain Res. Reviews*, 1998, 26, 236–242). Based on the localization of D3 receptors, it has also been suggested that D3 antagonists could be useful for the treatment of substance abuse (see, e.g., Levant, 1997, *Pharmacol. Rev.*, 49, 231–252). Conditions that can be treated by dopamine D3 receptor agonists include dyskinetic disorders such as Parkinson's disease, neurolepticinduced parkinsonism and tardive dyskinesias; depression; anxiety, memory disorders, sexual dysfunction and drug (e.g., cocaine) dependency.

In a further aspect, the present invention provides a method of treating conditions which require modulation of dopamine D3 receptors, for example anxiety, sexual dysfunction, movement disorders history of substance abuse or psychoses such as schizophrenia, which comprises administering to a subject in need thereof an effective amount of a compound of formula I or a physiologically acceptable salt thereof. The invention also provides the use of a compound of formula I or a physiologically acceptable salt thereof in the manufacture of a medicament for the treatment of conditions which require modulation of dopamine D3 receptors, for example anxiety, substance abuse, sexual dysfunction or psychoses such as schizophrenia.

A preferred use for D3 antagonists according to the present invention is in the treatment of anxiety and substance abuse. Preferred uses for D3 agonists according to the present invention are the treatment of dyskinetic disorders such as Parkinson's disease and treatment of sexual dysfunction, such as, for example, premature ejaculation.

For use as therapeutic agents, the compounds of the present invention are administered as a standard pharmaceutical composition., The present invention therefore provides in a further aspect pharmaceutical compositions comprising a novel compound of formula I or a physiologically acceptable salt thereof and a physiologically acceptable carrier. A The compounds of formula I can be administered by any convenient method, for example by oral, parenteral, buccal, sublingual, nasal, rectal or transdermal administration and the pharmaceutical compositions adapted accordingly. The compounds of formula I and their pharmaceutically acceptable salts that are active when given orally can be formulated as liquids or solids, for example syrups, suspensions or emulsions, tablets, capsules and lozenges. A liquid formulation will generally consist of a suspension or solution of the compound or pharmaceutically acceptable salt in a suitable liquid carrier(s) for example an aqueous solvent such as water, ethanol or glycerin, or a non-aqueous solvent, such as polyethylene glycol or an oil. The formulation may also contain a suspending agent, preservative, flavoring or coloring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration. Compositions for nasal administration may conveniently be formulated as aerosols, drops, gels and powders. Aerosol formulations typically comprise a solution or fine suspension of the active substance in a physiologically acceptable aqueous or nonaqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pumpatomiser. Compositions suitable for buccal or sublingual administration include tablets, lozenges and pastilles, wherein the active ingredient is formulated with a carrier such as sugar and acacia, tragacanth, or gelatin and glycerin. Compositions for rectal administration are conveniently in the form of suppositories containing a conventional suppository base such as cocoa butter. Compositions suitable for transdermal administration include ointments, gels and patches.

Generally, in carrying out the methods of this invention, the compounds of the formula I and their pharmaceutically acceptable salts will administered to an average adult human in amounts ranging from about 1 to about 1000 mg per day, in single or divided doses (i.e., from one to five doses per day), depending on the particular active agent, the age and condition of the patient and the the disorder for which the patient is being treated.

Preferably the composition is in unit dose form such as a tablet, capsule or ampoule. Each dosage unit for oral administration contains preferably from 1 to 250 mg (and for parenteral administration contains preferably from 0.1 to 25 mg) of a compound of the formula I or a physiologically acceptable salt thereof calculated as the free base.

Biological Test Methods

The ability of the compounds to bind selectively to human dopamine D3 receptors can be demonstrated by measuring their binding to cloned receptor. The inhibition constants ($K_i$) of test compounds were measured by displacement of [$^3$H] 7 OH-DPAT binding to membrane preparations from Chinese hamster ovary cells expressing human dopamine D3 receptor. Cells expressing the human D3 receptor were homogenized with Polytron and centrifuged for 10 min at 4° C. at 20,000 RPM in a Sorvall RCB5 centrifuge with a SS34 rotor. After repeating the washing once more, the pellet was resuspended in buffer consisting of 120 mM NaCl, 5 mM KCl, 5 mM MgCl$_2$, 2 mM CaCl$_2$ and 50 mM tris, pH 7.4 and the protein content determined using bovine serum albumin as a standard (Bradford, M. M. (1976) Anal. Biochem. 72, 248–254). Compounds at varying concentrations were incubated with the membrane preparations in the presence of 0.4 nM [$^3$H] 7 OH-DPAT. The assay was incubated for 15 min at 37° C. and the reaction was terminated by rapid filtration with 50 mM Tris pH 7.4, through GF/B filters previously soaked in 0.5% polyethyleneimine. Filters were dried overnight and counted in Betaplate Scintillation counter. Non-specific binding was defined as the radioligand binding remaining after incubation in the presence of 10 μM butacomol. For competition curves, seven concentrations (single log dilutions) of competing unlabeled, compounds were used. Competition curves were analysed simultaneously whenever possible using non-linear least-squares fitting procedures, capable of fitting one, two or three site models.

Binding data

| Compound | D3 Ki (nano molar) | D2 Ki (nano molar) |
| --- | --- | --- |
| [Z](+/−)2,6-Dimethyl-N-{2-[4-(3-trifluoromethyl-phenyl)-piperazin-1-ylmethyl]-cyclopropylmethyl}-benzamide; | 5 | 460 |
| [Z](+/−)N-{2-[4-(2-tert-Butyl-6-trifluoromethyl-pyrimidin-4-yl)-piperazin-1-ylmethyl]-cyclopropylmethyl}-2,6-dimethyl-benzamide; | 16 | >770 |
| [E](+/−)2,6-Dimethyl-N-{2-[4-(3-trifluoromethyl-phenyl)-piperazin-1-ylmethyl]-cyclopropylmethyl}-benzamide; | 2 | 76 |
| [Z](+/−)N-{2-[4-(2-tert-Butyl-6-trifluoromethyl-pyrimidin-4-yl)-piperazin-1-ylmethyl]-cyclopropylmethyl)-4-chloro-benzamide; | 31 | >740 |

Functional Activity at Cloned Dopamine D3 Receptor; The functional activity of compounds at human D3 receptor (i.e agonism or antagonism) were determined using an assays which monitored the agonist-induced binding of [$^{35}$S]-GTPγS in membrane preparation from Chinese hamster ovary cells expressing human dopamine D3 receptor. Cells expressing human D3 receptor were cultured in T175 flasks with medium containing DMEM and 10% fetal bovine serum. Cells were detached from the flask with 20 mM Hepes/10 mM EDTA and disrupted with a 22.5 gauge needle. After centrifugation at 40,000×g, the membranes were resuspended in 20 mM Hepes/0.1 mM EDTA and centrifuged again. Membranes were resuspended in assay buffer (20 mM Hepes, 100 mM NaCl, 10 mM MgCl$_2$) and incubated with 1 μM GDP on ice for 10 min. The test compounds were tested as agonists and antagonists in 96-well plates. Membranes and the test compounds were incubated for 20 min at 30° followed by 15 minutes incubation on ice. Unlabeled GTPγS (10 μM) was added in some wells to define non-specific binding. [$^{35}$S]-GTPγS was added at a final concentration of 0.1 nM, for 30 minutes incubation at 30° C. At this point, wheat germ agglutinin coated scintillation proximity beads were added to the assay (1 mg/well) and the assay plate shaken on a platform shaker for 30 minutes at room temperature. The plate was spun in a tabletop centrifuge for 5 minutes and counted on a Wallac Microbeta counter. Each concentration was set up as triplicate determinations. The agonist assay involved testing the compounds by themselves. The antagonist assay was performed in the presence of 100 nM dopamine. Functional potencies ($EC_{50}$ and functional $K_i$) were determined using a curve fitting software in PRISM.

The following experimental examples illustrate, but do not limit the scope of the present invention.

EXAMPLE 1

A. N-[[(Z)-2-(Hydroxymethyl)cyclopropyl]methyl]-2, 6dimethyl-benzamide

[(Z)-2-(Aminomethyl)cyclopropyl]methanol (2.0 g, 19.77 mmol), triethylamine (8.0 g, 79.09 mmol) in dichloromethane (20 ml) was cooled in an ice bath and 2,6-

Dimethyl-benzoyl chloride (3.3 g, 19.77 mmol) in dichloromethane (10 ml) was added dropwise over 10 min. After stirring for 16 hrs. at r.t., the reaction was concentrated, the residue was partitioned between ethyl acetate and water, the organics were washed with saturated sodium bicarbonate, dried over sodium sulfate and concentrated onto silica gel; flash chromatography using first an ethyl acetate/hexanes gradient followed by a methanol/chloroform/ammonium hydroxide gradient gave N-[[(Z)-2-(hydroxymethyl)cyclopropyl]methyl]-2,6-dimethyl-benzamide (2.35 g, 51%) as a yellow oil.

H$^1$ NMR CDCl$_3$ δ 7.12 (t, J=8 Hz, 1H), 6.98(d, J=8 Hz, 2H), 6.47(bs, 1H), 4.06–3.98(m, 1H), 3.92–3.83(m, 1H), 3.35–3.26(m, 1H), 3.13–3.04(m, 1H), 2.30(s, 6H), 1.30–1.02(m, 2H), 0.75(dq, J=5, 9, 14 Hz, 1H), 0.11 (q, J=5 Hz, 1H); MS=234.1(p+1).

B. 2,6-Dimethyl-N-{(Z)-2-[4-(3-trifluoromethyl-phenyl)-piperazin-1-ylmethyl]-cyclopropylmethyl}benzamide N-[[(Z)-2-(Hydroxymethyl)cyclopropyl]methyl]-2,6-dimethyl-benzamide (0.25 g, 1.07 mmol), triethylamine (0.32 g, 3.21 mmol) and dichloromethane (10 ml) was cooled in an ice bath and methanesulfonic anhydride (0.28 g, 1.61 mmol) and dichloromethane (10 ml) was added dropwise over 15 min. After stirring for 1 hr. at 0° C., the reaction was warmed to ambient temperature and stirred for 2 hrs., then 1-(α, α, α-trifluoro-m-tolyl)piperazine hydrochloride (0.29 g, 1.07 mmol) was added all in one portion. After addition, the reaction was heated to 85° C. (external temperature) and refluxed for 16 hrs. The reaction was cooled to ambient temperature, then concentrated onto silica gel; flash chromatography using an ethyl acetate/hexanes gradient gave 2,6-dimethyl-N-{(Z)-2-[4-(3-trifluoromethyl-phenyl)-piperazin-1-ylmethyl]-cyclopropylmethyl}benzamide (0.097 g, 20%) as a colorless oil. The product was converted to the dihydrochloride salt in dichloromethane with HCl gas to yield a white solid (0.080 g).

H$^1$ NMR CDCl$_3$ δ 11.14(bs, 1H), 8.49(m, 1H), 7.44(t, J=8 Hz, 1H), 7.31–7.20(m, 2H), 7.17–7.08(m, 2H), 7.00(d, J=8 Hz, 2H), 3.95(d, J=13 Hz, 2H), 3.65–3.02(m, 11H), 2.19(s, 6H), 1.32–1.16(m, 2H), 0.92–0.84(m, 1H), 0.48–0.40(m, 1H); MS=446.1(p+1).

EXAMPLE 2

N-[[(E)-2-(Hydroxymethyl)cyclopropyl]methyl]-2,6-dimethyl-benzamide

The above compound was prepared using the same general procedure that was used to synthesize N-[[(Z)-2-(Hydroxymethyl)cyclopropyl]methyl]-2,6-dimethyl-benzamide in Example 1A.

NMR CDCl$_3$ δ 7.20–7.14(m, 1H), 7.05–6.97(m, 2H), 5.60(bs, 1H), 4.21–4.07(m, 2H), 3.22–3.07(m, 2H), 2.31(s, 6H), 1.21–0.98(m, 2H), 0.64–0.54(m, 2H); MS=234.3(p+1).

EXAMPLE 3

2,6-Dimethyl-N-{(E)-2-[4-(3-trifluoromethyl-phenyl)-piperazin-1-ylmethyl]-cyclopropylmethyl}benzamide A. N-[(E)-2-(Bromomethyl)cyclopropylmethyl]-2,6-dimethyl-benzamide N-[[(E)-2-(Hydroxymethyl)cyclopropyl]methyl]-2,6-dimethyl-benzamide (1.5 g, 6.43 mmol), 48% hydrobromic acid (1.5 ml) and benzene (50 ml) were refluxed for 16 hrs. using a Dean & Stark receiver. The yellow solution was diluted with ethyl acetate (50 ml) and washed with saturated sodium bicarbonate, water, brine and dried over sodium sulfate. Concentration yielded N-[(E)-2-(Bromomethyl)cyclopropylmethyl]-2,6-dimethyl-benzamide (0.7 g, 37%) as a brown oil which was used without purification.

H$^1$ NMR CDCl$_3$ δ 7.21–6.88(m, 3H), 4.21–4.07(m, 1H), 3.44–3.29(m, 1H), 2.36–2.20(m, 6H), 1.32–1.10(m, 1H), 0.84–0.54(m, 2H).

B. 2,6-Dimethyl-N-{(E)-2-[4-(3-trifluoromethyl-phenyl)-piperazin-1-ylmethyl]-cyclopropylmethyl}benzamide N-[(E)-2-(Bromomethyl)cyclopropylmethyl]-2,6-dimethyl-benzamide (0.7 g, 2.36 mmol), 1-(α, α, α-trifluoro-m-tolyl)piperazine hydrochloride (1.3 g, 4.73 mmol), sodium carbonate (1.3 g, 11.82 mmol) and acetonitrile (20 ml) were refluxed for 24 hrs. The mixture was concentrated, redissolved in ethyl acetate and washed with water, brine, dried over magnesium sulfate and concentrated on to silica gel; flash chromatography using first an ethyl acetate/hexanes gradient followed by methanol/chloroform/ammonium hydroxide gradient gave 2,6-dimethyl-N-{(E)-2-[4-(3-trifluoromethyl-phenyl)-piperazin-1-ylmethyl]-cyclopropylmethyl}benzamide (0.06 g, 6%) as a light brown oil. The product was converted to the dihydrochloride salt in dichloromethane with HCl gas to yield a white solid (0.041 g). NMR DMSO δ 10.75(bs, 1H), 8.60–8.40(m, 1H), 7.36–6.98 (m, 6H), 3.97(bd, J=12 Hz, 2H), 3.45–2.92(m, 10H), 2.24(s, 6H), 1.23–1.04(m, 2H), 0.77–0.60(m, 2H); MS=446.1(p+1).

EXAMPLE 4

N-{(Z)-2-[4-(2-tert-Butyl-6-trifluoromethyl-pyrimidin-4-yl)-piperazin-1-ylmethyl]-cyclopropylmethyl}-2,6-dimethyl-benzamide, dihydrochloride salt:

The title compound was prepared using the a procedure analogous to that described in Example 3.

H$^1$ NMR DMSO δ 11.37(bs, 1H), 8.48(bs, 1H), 7.23–6.93 (m, 4H), 3.74–2.94(m, 10H), 2.35–2.00(m, 7H), 1.43–0.99 (m, 10H), 0.95–0.00(m, 3H); Analysis calculated for C$_{27}$H$_{36}$F$_3$N$_5$O.2HCl.H$_2$O: C, 56.25; H, 6.64; N, 12.15. Found: C, 57.36; H, 6.73; N, 11.41.

The invention claimed is:

1. A compound of the formula

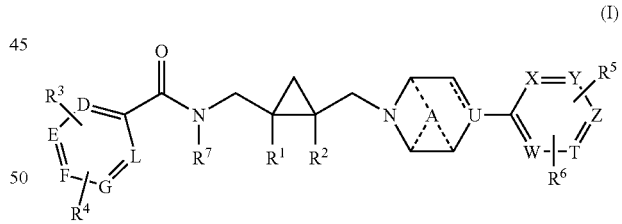

(I)

wherein D, E, F, G, L, T, W, X, Y and Z are each, independently, N or CH;

U is N and U is single bonded to both carbons adjacent to it in the nitrogen containing ring of which it is a member;

A is (CH$_2$)$_m$ wherein m is zero and the dashed lines attached to A are absent;

R$^1$ and R$^2$ are selected, independently, from hydrogen, (C$_1$–C$_6$) alkyl optionally substituted with from one to seven fluorine atoms, cyano, —OR$^9$, and —CONHR$^{10}$;

R$^3$ and R$^4$ are selected, independently, from hydrogen, halo, (C$_1$–C$_6$) alkyl optionally substituted with from one to seven fluorine atoms, cyano, hydroxy, —CONHR$^{11}$, —OR$^{12}$, —NR$^{13}$R$^{14}$ and —COR$^{15}$;

R⁵ and R⁶ are selected, independently, from hydrogen, halo, (C₁–C₆) alkyl optionally substituted with from one to seven chlorine atoms, cyano, hydroxy, —CONHR¹⁶, —OR¹⁷, —NR¹⁸R¹⁹, and —COR²⁰, R⁷ is hydrogen, (C₁–C₆) alkyl optionally substituted with from one to seven fluorine atoms, or aryl selected from phenyl and naphthyl, wherein said aryl can be optionally substituted with from one to three substituents independently selected from (C₁–C₄) alkyl optionally substituted with from one to three fluorine atoms, (C₁–C₄) alkoxy optionally substituted with from one to three fluorine atoms, cyano, nitro, halo, hydroxy, amino, (C₁–C₄) alkylamino, di[(C₁–C₆) alkyl]amino, (C₁–C₄) amidoamino and (C₁–C₄) alkanoyl;

R⁸ is selected from hydrogen, cyano, (C₁–C₆) alkyl optionally substituted with from one to seven fluorine atoms, —OR⁹, and —CONHR¹⁰;

R⁹, R¹⁰, R¹¹, R¹², R¹³, R¹⁴, R¹⁶, R¹⁷, R¹⁸ and R¹⁹ are selected, independently, from hydrogen, (C₁–C₆) alkyl optionally substituted with from one to seven fluorine atoms and, aryl wherein said aryl is selected from phenyl and naphthyl and wherein said aryl can optionally be substituted with one or more substitituents, preferably with from zero to two substituents, independently selected from (C₁–C₄) alkyl optionally substituted with from one to three fluorine atoms, (C₁–C₄) alkoxy optionally substituted with from one to three fluorine atoms, cyano, nitro, halo, hydroxy, amino, (C₁–C₄) alkylamino, di[(C₁–C₆)alkyl] amino, (C₁–C₄) amidoamino and (C₁–C₄) alkanoyl;

R¹⁵ and R²⁰ are selected, independently, from NHR²¹ and the group of radicals listed in the definition of R⁹ through R¹⁹; and R²¹ is selected from the group of radicals listed in the definition of R⁹ through R¹⁹;

or a pharmaceutically acceptable salt thereof, with the proviso that ring D, E, F, G, L and ring T, W, X, Y, and Z are each independently pyrimidyl, or phenyl rings.

2. A compound according to claim 1, wherein both R¹ and R² are hydrogen.

3. A compound according to claim 1, wherein R¹ and R² are selected, independently, from hydrogen and (C₁–C₆) alkyl.

4. A compound according to claim 1 which is in the Z (cis) configuration with respect to the cyclopropyl ring.

5. A compound according to claim 1 wherein the compound is:

[Z](+/−)N-{2-[4-(2-tert-Butyl-6-trifluoromethyl-pyrimidin-4-yl)-piperazin-1-ylmethyl]-cyclopropylmethyl}-2,6-dimethyl-benzamide;

[Z](+/−)N-{2-[4-(2-tert-Butyl-6-trifluoromethyl-pyrimidin-4-yl)-piperazin-1-ylmethyl]-cyclopropylmethyl}-4-chloro-benzamide;

[Z](+/−)N-{2-[4-(2-tert-Butyl-6-trifluoromethyl-pyrimidin-4-yl)-piperazin-1-ylmethyl]-cyclopropylmethyl}-2,4,6-trimethyl-benzamide;

[Z](+/−)N-{2-[4-(2-tert-Butyl-6-trifluoromethyl-pyrimidin-4-yl)-piperazin-1-ylmethyl]-cyclopropylmethyl}-3,4-dimethyl-benzamide;

[Z](+/−)N-{2-[4-(2-tert-Butyl-6-trifluoromethyl-pyrimidin-4-yl)-piperazin-1-ylmethyl]-cyclopropylmethyl}-3,5-dimethoxy-benzamide;

[Z](+/−)N-{2-[4-(2-tert-Butyl-6-trifluoromethyl-pyrimidin-4-yl)-piperazin-1-ylmethyl]-cyclopropylmethyl}-3-fluoro-benzamide;

[Z](+/−)N-{2-[4-(2-tert-Butyl-6-trifluoromethyl-pyrimidin-4-yl)-piperazin-1-ylmethyl]-cyclopropylmethyl}-2-methyl-benzamide;

[Z](+/−)N-{2-[4-(2-tert-Butyl-6-trifluoromethyl-pyrimidin-4-yl)-piperazin-1-ylmethyl]-cyclopropylmethyl}-2,3-dimethyl-benzamide;

[Z](+/−)N-{2-[4-(2-tert-Butyl-6-trifluoromethyl-pyrimidin-4-yl)-piperazin-1-ylmethyl]-cyclopropylmethyl}-3,4-dimethoxy-benzamide;

[Z](+/−)N-{2-[4-(2-tert-Butyl-6-trifluoromethyl-pyrimidin-4-yl)-piperazin-1-ylmethyl]-cyclopropylmethyl}-3,4,5-trimethoxy-benzamide;

[Z](+/−)N-{2-[4-(2-tert-Butyl-6-trifluoromethyl-pyrimidin-4-yl)-piperazin-1-ylmethyl]-cyclopropylmethyl}-4-fluoro-benzamide;

[Z](+/−)N-{2-[4-(2-tert-Butyl-6-trifluoromethyl-pyrimidin-4-yl)-piperazin-1-ylmethyl]-cyclopropylmethyl}-3-chloro-benzamide;

[Z](+/−)N-{2-[4-(2-tert-Butyl-6-trifluoromethyl-pyrimidin-4-yl)-piperazin-1-ylmethyl]-cyclopropylmethyl}-4-trifluoromethyl-benzamide;

[Z](+/−)N-{2-[4-(2-tert-Butyl-6-trifluoromethyl-pyrimidin-4-yl)-piperazin-1-ylmethyl]-cyclopropylmethyl}-3-cyano-benzamide;

[Z](+/−)N-{2-[4-(2-tert-Butyl-6-trifluoromethyl-pyrimidin-4-yl)-piperazin-1-ylmethyl]-cyclopropylmethyl}-2,6-dimethyl-benzamide;

[Z](+/−)N-{2-[4-(2-tert-Butyl-6-trifluoromethyl-pyrimidin-4-yl)-piperazin-1-ylmethyl]-cyclopropylmethyl}-2,4-difluoro-benzamide;

[Z](+/−)N-{2-[4-(2-tert-Butyl-6-trifluoromethyl-pyrimidin-4-yl)-piperazin-1-ylmethyl]-cyclopropylmethyl}-2,3-difluoro-benzamide;

[Z](+/−)N-{2-[4-(2-tert-Butyl-6-trifluoromethyl-pyrimidin-4-yl)-piperazin-1-ylmethyl]-cyclopropylmethyl}-2-trifluoromethyl-benzamide;

[Z](+/−)N-{2-[4-(2-tert-Butyl-6-trifluoromethyl-pyrimidin-4-yl)-piperazin-1-ylmethyl]-cyclopropylmethyl}-2,5-dichloro-benzamide;

[Z](+/−)N-{2-[4-(2-tert-Butyl-6-trifluoromethyl-pyrimidin-4-yl)-piperazin-1-ylmethyl]-cyclopropylmethyl}-2,3-dichloro-benzamide;

[Z](+/−)N-{2-[4-(2-tert-Butyl-6-trifluoromethyl-pyrimidin-4-yl)-piperazin-1-ylmethyl]-cyclopropylmethyl}-2,4-dimethyl-benzamide;

[Z](+/−)N-{2-[4-(2-tert-Butyl-6-trifluoromethyl-pyrimidin-4-yl)-piperazin-1-ylmethyl]-cyclopropylmethyl}-3-chloro-2-fluoro-benzamide;

[Z](+/−)N-{2-[4-(2-tert-Butyl-6-trifluoromethyl-pyrimidin-4-yl)-piperazin-1-ylmethyl]-cyclopropylmethyl}-2-chloro-4-fluoro-benzamide;

[Z](+/−)N-{2-[4-(2-tert-Butyl-6-trifluoromethyl-pyrimidin-4-yl)-piperazin-1-ylmethyl]-cyclopropylmethyl}-2,4-dichloro-benzamide; and N-{2-[4-(2-tert-Butyl-6-trifluoromethyl-pyrimidin-4-yl)-piperazin-1-ylmethyl]-cyclopropylmethyl}-4-diethylamino-benzamide.

6. A compound according to claim 1 wherein R¹ and R² are selected, independently, from hydrogen, methyl, cyano, trifluoromethyl and trifluoromethoxy.

7. A compound according to claim 1 wherein the compound is:

[Z](+/−)2,6-Dimethyl-N-{2-[4-(3trifluoromethyl-phenyl)-piperazin-1-ylmethyl]-cyclopropylmethyl}-benzamide; and

[E](+/−)2,6-Dimethyl-N-{2-[4-(3trifluoromethyl-phenyl)-piperazin-1-ylmethyl]-cyclopropylmethyl}-benzamide.

8. A pharmaceutical composition for treating a disorder or condition selected from psychotic disorders, and Parkinson's disease in a mammal, comprising an amount of a compound according to claim 1, or a pharmaceutically acceptable salt thereof, that is effective in treating such disorder or condition, and a pharmaceutically acceptable carrier.

9. A method of treating a disorder or condition selected from psychotic disorders, and Parkinson's disease in a mammal, comprising administering to said mammal an amount of a compound according to claim 1, or a pharmaceutically acceptable salt thereof, that is effective in treating such disorder or condition.

10. A method according to claim 9 wherein the disorder or condition being treated is a psychotic disorder or condition.

11. A method according to claim 9 wherein the disorder or condition being treated is Parkinson's disease.

* * * * *